(12) United States Patent
Gutfleisch et al.

(10) Patent No.: US 8,923,475 B2
(45) Date of Patent: Dec. 30, 2014

(54) SYSTEM AND METHOD FOR RECORDING CONE-BEAM TOMOGRAMS IN RADIATION THERAPY

(75) Inventors: Marcus Gutfleisch, Leimen (DE);
Thomas Tücking, Röttenbach (DE);
Douglas Howard, Antioch, CA (US);
Edward Lewis Calderon, Pittsburg, CA (US)

(73) Assignees: Siemens Aktiengesellschaft, München (DE); Siemens Medical Solutions USA, Inc., Malvern, PA (US)

( * ) Notice: Subject to any disclaimer, the term of this patent is extended or adjusted under 35 U.S.C. 154(b) by 361 days.

(21) Appl. No.: 13/363,307

(22) Filed: Jan. 31, 2012

(65) Prior Publication Data

US 2013/0193349 A1      Aug. 1, 2013

(51) Int. Cl.
G01N 23/04      (2006.01)
A61B 6/03      (2006.01)
A61B 6/00      (2006.01)

(52) U.S. Cl.
CPC .............. *G01N 23/046* (2013.01); *A61B 6/032* (2013.01); *A61B 6/4476* (2013.01); *A61B 6/54* (2013.01); *G01N 2223/306* (2013.01); *G01N 2223/3303* (2013.01)
USPC ................................................. 378/4; 378/91

(58) Field of Classification Search
CPC ...... A61B 6/032; A61B 6/035; A61B 6/4085; A61B 6/4476; A61B 6/54; A61B 6/541; G01N 23/046; G01N 2223/306; G01N 2223/3303; H05G 1/30

USPC .......................................................... 378/4, 91
See application file for complete search history.

(56) References Cited

U.S. PATENT DOCUMENTS

| | | | | |
|---|---|---|---|---|
| 5,027,380 A * | 6/1991 | Nishiki | ............................. | 378/4 |
| 5,291,402 A * | 3/1994 | Pfoh | .............................. | 378/13 |
| 5,991,358 A * | 11/1999 | Dolazza et al. | ................ | 378/19 |
| 6,047,040 A * | 4/2000 | Hu et al. | .......................... | 378/19 |
| 6,553,091 B2 * | 4/2003 | Takanashi et al. | .............. | 378/15 |
| 6,574,301 B1 * | 6/2003 | Jansen | ............................ | 378/20 |
| 7,447,297 B2 * | 11/2008 | Dunham et al. | ............. | 378/113 |
| 7,460,635 B2 * | 12/2008 | Fujimoto et al. | .................. | 378/8 |
| 7,545,907 B2 * | 6/2009 | Stewart et al. | ................... | 378/37 |
| 7,649,974 B2 * | 1/2010 | Arenson et al. | .................. | 378/16 |
| 7,945,021 B2 * | 5/2011 | Shapiro et al. | .................. | 378/65 |

* cited by examiner

*Primary Examiner* — Allen C. Ho
(74) *Attorney, Agent, or Firm* — Lempia Summerfield Katz LLC (57) ABSTRACT

A system for motion control of a cone-beam tomography recording device includes a drive system configured to position a paired radiation source and radiation detector relative to an object. The system further includes a controller configured to: initiate a trigger plan operable as a function of a constant frequency control signal, activate the paired radiation source and radiation detector in accordance with the trigger plan, drive, in response to the trigger plan, the first drive system to a steady operating state derived as a function of the constant frequency, capture a plurality of broadcast radiation signals representative of a plurality of two dimensional images of the object such that the two dimensional images are defined equidistant positions defined by the trigger plan and as a function of the constant frequency signal, and generate a three dimensional representation of the object based on the plurality of two dimensional images.

17 Claims, 5 Drawing Sheets

SYSTEM AND METHOD FOR RECORDING CONE-BEAM TOMOGRAMS IN RADIATION THERAPY

TECHNICAL FIELD

This patent document discloses and generally relates to a system, method and functionality for synchronizing and/or controlling the relative movement of a radiation source and a detector utilized to record and capture images in a cone-beam tomography application.

BACKGROUND

Conventional cone-beam computed tomography systems incorporate a radiation source and radiation detector combination that can be positioned at specific locations around an object to be imaged. In operation, the information and data gather by the radiation source and radiation detector combination at each specific location is analyzed to generate a three-dimensional (3D) representation of the object to be imaged. In particular, the radiation source and radiation detector combination processes a plurality of projection images to create and construct the three-dimensional (3D) representation. The specific locations at which each projection image is acquired are provided by a motion control signal or control signal generated by a motor or drive controller. The motion control signal or control signal generated by conventional systems defines equidistantly spaced angular positions along a circular path followed by the moving radiation source and radiation detector combination. The plurality of projection images acquired at different angular positions in response to the motion control signal is then reconstructed via a conventional three-dimensional reconstruction technique such as filtered back-projection.

In operation, the plurality of projection images acquired at different angular positions may not be chronologically equidistant due to irregular or uncontrolled motion of the radiation source and radiation detector combination. For example, the radiation detector may have non-ideal properties that vary based on the chronological triggering of the radiation source and can result in degraded image quality. These variations in the chronological triggering of the radiation source can result in geometric distortions in the resulting three dimensional reconstruction of the object to be imaged. In an attempt to address and compensate for these geometric distortions, the radiation detector utilized in conventional systems is calibrated for different time schemes in order to address a wide range of possible imaging situations. However, these compensations require a compromise between the calibration effort and the overall image quality of the object to be imaged.

DETAILED DESCRIPTION

The disclosed cone-beam computed tomography system addresses and overcomes the distortions and inaccuracies endemic in conventional systems by controlling the radiation source and radiation detector combination as a function of one or more spatial positions. In other words, the disclosed cone-beam computed tomography system enables, suppresses or terminates the operation of the radiation source and radiation detector combination based on a known or detected position relative to the object to be imaged. The operation of the radiation source and radiation detector combination is controlled by a trigger or trigger plan based on a constant frequency. For example, by utilizing a trigger or trigger plan based on a constant frequency timing pulse, the radiation detector may be operated within a fixed time plan, resulting in a simplified calibration process as well as improved image quality.

In operation, the trigger or trigger plan that controls and/or directs the operation of the radiation source and radiation detector combination may be initiated prior to the mechanical motion of the system. In this way, the system reaches a steady or stable operating state before the imaging process begins, resulting in the generation and capture of substantially equidistant spatial projections.

I. System Overview

Figure 1:
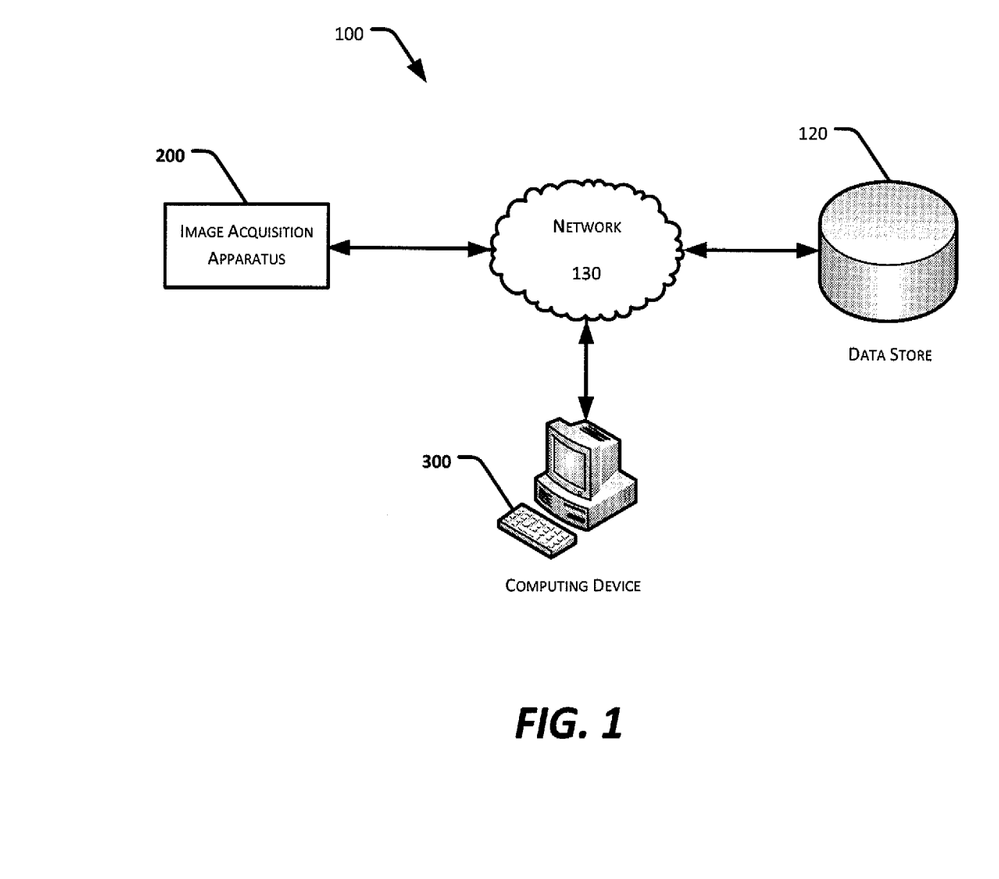
FIG. 1 is a general overview of an exemplary cone-beam computed tomography system configured according to the teaching and disclosure provided herein.

FIG. 1 provides a general overview of a system 100 for an exemplary cone-beam computed tomography system and process that may be implemented to accurately image an object of interest. The exemplary cone-beam computed tomography system 100 may be an ARITISTE™ system manufactured by Siemens Industry, Inc., Healthcare Division (hereinafter referred to as "Siemens"). The displayed representation is intended to illustrate one possible configuration of the cone-beam computed tomography system 100. Other configuration can include fewer components, and in other configurations, additional components may be utilized. Variations in the arrangement and type of these components may be made without departing from the spirit or scope of the claims as set forth herein. These changes in configurations and components can increase or alter the capabilities of the cone-beam computed tomography system 100.

The exemplary cone-beam computed tomography system 100 includes an image acquisition apparatus 200, a data store 120, a network 130 and a computing device 300. The image acquisition apparatus 200 may include elements and components necessary to generate and capture radiation signals directed at an object to be imaged. The captured radiation signals acquired from a plurality of locations relative to the object to be imaged may, in turn, be communicated to the data store 120 via the network 130. The stored radiation signals represent image data and information captured in connection with the object to be imaged. The computing device 300, in this embodiment, can process the stored radiation signals and analyze the image data to generate a three dimensional representation of the object. The computing device 300 may further display and provide an operator interface for use by an operator.

A. Image Acquisition Device

Figure 2:
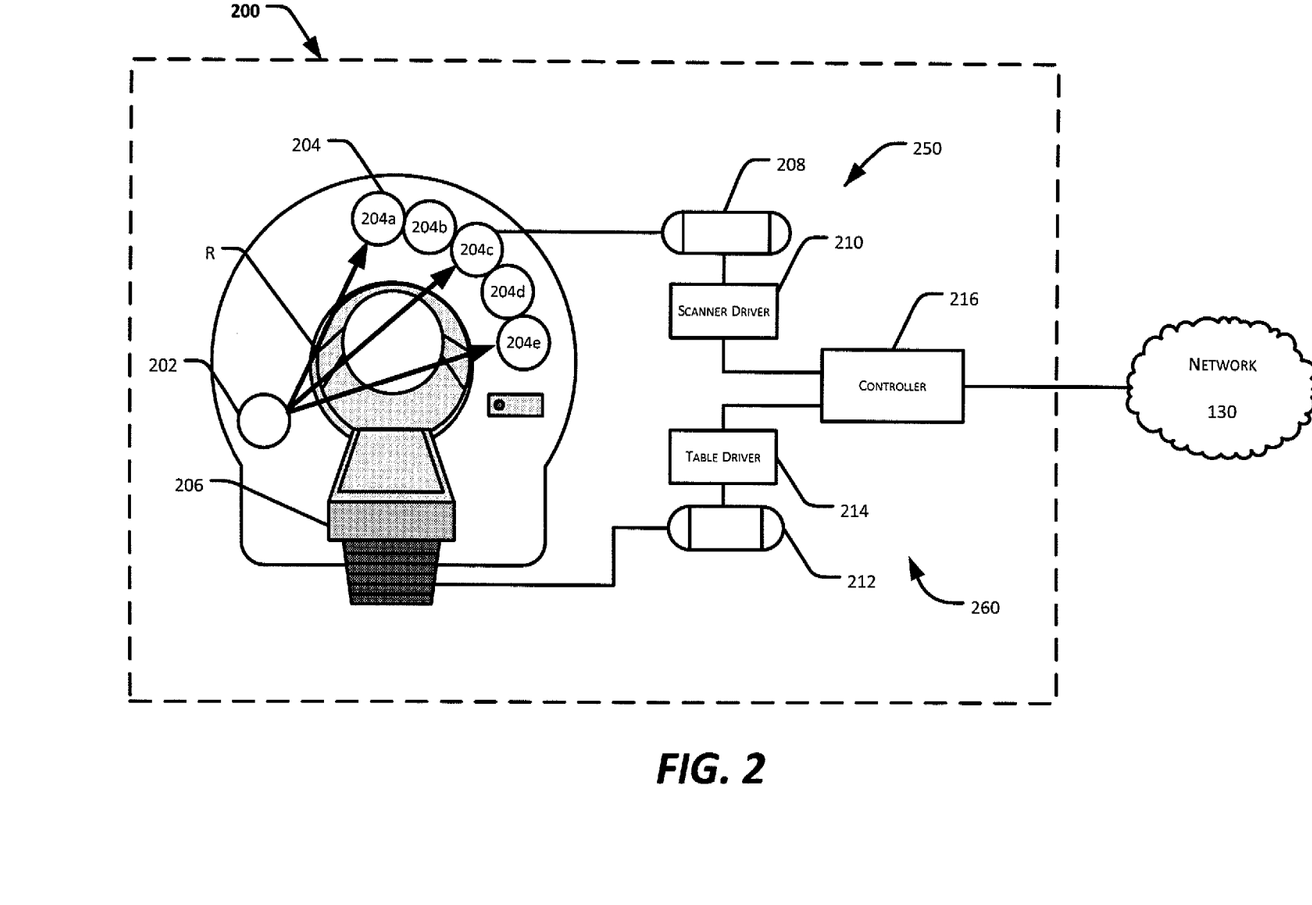
FIG. 2 illustrates an exemplary image acquisition apparatus that may be utilized in conjunction with the system shown in FIG. 1.

As shown in FIG. 2, the image acquisition apparatus 200 includes a radiation source 202 and a radiation detector 204 including a plurality of sensors 204a to 204e that may be arranged around and adjacent to the object to be imaged. For example, the radiation source 202 may be placed adjacent to a first side of the object and directed towards the radiation detector 204 placed adjacent to a second and opposite side of the object. In this way, when the radiation source 202 generates and emits a radiation signal (generally indicated by the arrows R), the radiation detector 204 is positioned to receive the signal once the signal has passed through the object.

The image acquisition apparatus 200 may further include a first drive system 250 mechanically coupled to the radiation source 202 and the radiation detector 204 combination, and a second drive system 260 mechanically coupled to a patient positioning table 206 positioned substantially orthogonal to the plane defined by the radiation source 202 and the radiation detector 204 combination. The patient positioning table 206 is configured to translate and adjust the position of a patient or other object to be imaged relative to the emitted radiation signals R. The first and second drive systems 250 and 260 may be configured to precisely position the imaging elements (e.g., the radiation source 202 and the radiation detector 204 combination) relative to the patient positioning table 206 supporting the object to be imaged. In this configuration, the imaging elements and the object to be imaged supported by the positioning table 206 may be independently positioned relative to each other to allow for a plurality of radiation R, and subsequently image data, to be captured at different relative positions and aspects.

The first drive system 250 may further include a motor 208 paired with a motor driver 210. Similarly, the second drive system 260 may further include a motor 212 paired with a motor driver 214. The motor drivers 210 and 214 are, in turn, arranged in communication with a controller 216. The controller 216 may be configured and programmed to execute a trigger or tripping plan that controls the activation and operation of the imaging elements represented by the radiation source 202 and the radiation detector 204. Conventional tomography systems typically implement tripping plans to activate the imaging elements based on the angular position of the radiation source 202 and radiation detector 204 combination. For example, a conventional system may activate the imaging elements once per degree of angular motion based on a timed motor acceleration and deceleration profile. Imprecision in timing and motor performance can result in image degradation caused due to non-uniform position and capture of the plurality of radiation signals R used to construct the resulting three dimensional image. As disclosed herein, the cone-beam computed tomography system 100 implements a tripping plan based on a constant frequency control signal generated and provided by the controller 216. Activation of the disclosed cone-beam computed tomography system 100 by the tripping plan implemented by the controller 216 may cause the radiation detector 204 to power-up or activate to receive the plurality radiation signals R generated and broadcast by the radiation source 202.

In operation, the controller 216 may direct the first drive system 250 to position the radiation source 202 and radiation detector 204 combination at a desired location based on the received constant frequency control signal. The regular oscillation (e.g., the high frequency variation or changes between each peak and valley of the signal) of the control signal may be detected and accumulated to precisely direct the activation and deactivation of the motor 208 and driver 210. In this way, the controller 216 may direct the motor driver 210 to activate the motor 208 for a specific and/or pre-defined number of clock pulses. The constant frequency control signal provides a highly precise mechanism by which the radiation source 202 and radiation detector 204 combination may be positioned.

The motor driver 210 may be a separate component as illustrated in FIG. 2 or may be integral to the motor 208. In this exemplary embodiment, the motor driver 210 is in communication with the controller 216 and configured to receive the control information therefrom. The motor driver 210, in turn, converts and/or translates the control information into electrical pulses and potentials necessary to drive the motor 208. The motor driver 214 may similarly be in communication with the controller 216 and configured to operate as a translation bridge between the controller 216 and the motor 212 driving the patient positioning table 206.

The controller 216 may further be configured to generate and provide the same constant frequency control signal to each of the drive systems 250 and 260. The constant frequency control signal can be generated by the controller 216 or may be provide by another component or system operable within the cone-beam computed tomography system 100.

B. Data Store

The data store 120 may be operative to store detected radiation signals and the associated image data captured around the object to be imaged. The stored information may further be cross-referenced and/or correlated to a position and time at which each signal was transmitted and received. Other data related to the cone-beam computed tomography system 100 may be accessibly stored by the data store 120. For example, the data store 120 may previously capture radiation signals and image data, alternate trigger or tripping plans, and different performance or operating parameters and characteristics for each of the motors 208 and 212.

The data store 120 represents one or more relational databases or other data stores managed using various known database management techniques, such as, for example, SQL and object-based techniques. The data store 120 implements using one or more magnetic, optical, solid state or tape drives, or other storage mediums available now or later developed.

In this embodiment the data store 120 is shown in communication with the computing device 300 via the network 130. In this configuration, the data store 120 implements as a database server running MICROSOFT SQL SERVER®, ORACLE®, IBM DB2® or any other database software. The data store 120 may further be in communication with other computing devices and servers through the network 130.

C. Network

The network 130 may include wide area networks (WAN), such as the Internet, local area networks (LAN), campus area networks, metropolitan area networks, or any other networks that may facilitate data communication. The network 130 may be divided into sub-networks that allow access to all of the other components connected to the network 130 in the cone-beam computed tomography system 100. Alternatively, the sub-networks may restrict access between the components connected to the network 130. The network 130 may be configured as a public or private network connection and may include, for example, a virtual private network or an encryption scheme that may be employed over the public Internet.

D. Computing Device

The computing device 300 may be connected to the network 130 in any configuration that supports data transfer. These configurations include both wired and wireless data connections to the network 130. The computing device 300 can further run a web application on any platform that supports web content, such as a web browser or a computer, a mobile phone, personal digital assistant (PDA), and/or any appliance or device capable of data communications.

Figure 3:
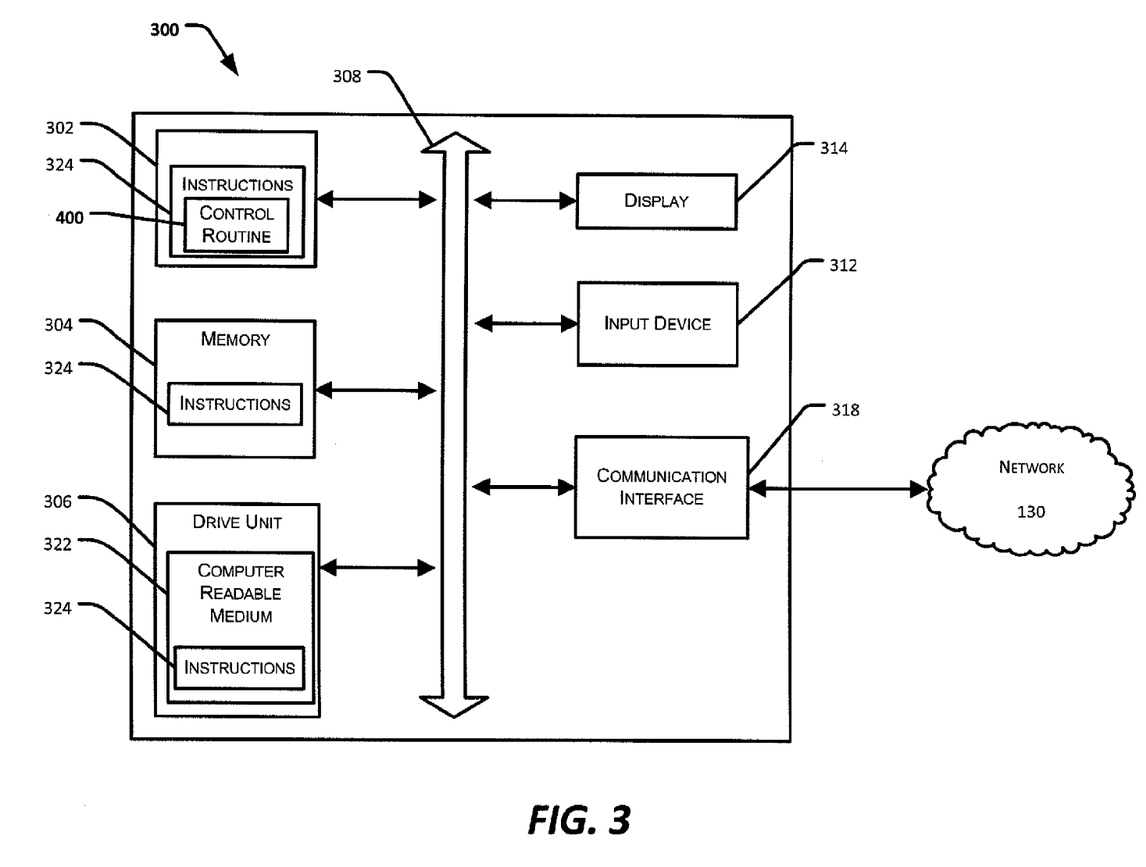
FIG. 3 illustrates a general computer system that may be used in the system shown in FIG. 1, or other cone-beam computed tomography systems.

The computing device 300 will typically include a processor, memory, a display, a user interface and a communication interface. The processor may be operatively coupled with the memory, the display and the interfaces and may perform tasks at the request of the standalone application or the underlying operating system. Herein, the phrases "coupled with", "in communication with" and "connected to" may be defined to be components arranged to directly or indirectly exchange information, data and commands through one or more intermediate components. The intermediate components may include both hardware and software based components.

The memory represents any hardware configuration capable of storing data. The display operatively couples to the memory and the processor in order to display information to the operator. The user interface, in turn, is stored in the memory and executed by the processor for display via the display. The user interface provides a mechanism by which an operator can interact with the system and matching programs and algorithms. From the above descriptions, it is to be inferred that the system and method for progressive feature evaluation are highly adaptable and configurable. The flexible nature of the disclosed system and method allow for a wide variety of implementations and uses for the discussed and disclosed technology and algorithms.

Herein, the phrase "operatively coupled" is defined to be two or more devices configured to share resources or information either directly or indirectly through one or more intermediate components. The communication interface may be operatively coupled with the memory, and the processor, and may be capable of communicating through the network 130 with the image acquisition apparatus 200. The standalone application may be programmed in any programming language that supports communication protocols. Examples of these languages include: SUN JAVA®, C++, C#, ASP, SUN JAVASCRIPT®, asynchronous SUN JAVASCRIPT®, or ADOBE FLASH ACTION SCRIPT®, amongst others.

The computing device 300 may be any mobile device that has a data connection and may run a mobile application. The data connection may be a cellular connection, a wireless data connection, an Internet connection, an infrared connection, a Bluetooth connection, or any other connection capable of transmitting data. For example, the mobile application may be an application running on an iPhone™ available from Apple, Inc.

E. Computing System Layout

FIG. 3 illustrates a layout and configuration for a generalized computing device 300, or any of the other computing devices and motor drivers referenced herein. The computing device 300 stores and executes algorithms and processor-executable instructions 324 to cause the performance of any one or more of the methods or computer based functions discussed and disclosed in this patent document. For example, the processor-executable instructions 324 can include a constant frequency control routine 400 (see FIG. 4) to direct and control the operation of the first and second drive systems 250 and 260, as well as the imaging elements. The computing device 300 may operate as a standalone device or may be connected to other computer systems or peripheral devices.

In a networked deployment, the computing device 300 may operate in the capacity of either a server or a client computer in a server-client network environment, or as a peer computer system in a peer-to-peer (or distributed) network environment. The computing device 300 may also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a web appliance, a network router, a switch or bridge, or any other machine capable of executing the processor-executable instructions 324 (sequential or otherwise) that specify actions to be taken by that machine. In a particular embodiment, the computing device 300 may be implemented using electronic devices that provide voice, video or data communication. Further, while a single computing device 300 may be illustrated, the term "system" shall also be taken to include any collection of systems or subsystems that individually or jointly execute a set or multiple sets of processor-executable instructions to perform one or more functions via the network 130.

The computing device 300 includes a processor 302 such as a central processing unit (CPU), a graphics-processing unit (GPU), or both. The processor 302 may be a component in a variety of systems. For example, the processor 302 may be part of a standard personal computer or a workstation. The processor hardware may incorporate one or more general processors, digital signal processors (DSPs), application specific integrated circuits (ASICs), field programmable gate arrays (FPGAs), servers, networks, digital circuits, analog circuits, combinations thereof, or other now known or later developed devices for analyzing and processing data.

The computing device 300 may include a memory 304 that can communicate via a bus 308. The memory 304 can be divided or segmented into, for example, a main memory, a static memory, and a dynamic memory. The memory 304 includes, but may not be limited to, computer readable storage media and various types of volatile and non-volatile storage media such as: random access memory; read-only memory; programmable read-only memory; electrically programmable read-only memory; electrically erasable read-only memory; flash memory; magnetic tape or disk; optical media and the like. In one case, the memory 304 includes a cache or random access memory for the processor 302. Alternatively, or in addition to, the memory 304 may be system memory that is separated and/or distinct from the processor 302.

The memory 304 may be an external storage device or database for storing data. Examples include a hard drive, compact disc ("CD"), digital video disc ("DVD"), memory card, memory stick, floppy disc, universal serial bus ("USB") memory device, or any other device operative to store data. The memory 304 is configured to store processor-executable instructions 324 utilizable by the processor 302. The functions, acts or tasks illustrated in the figures or described herein may be performed by the programmed processor 302 executing the instructions 324 stored in the memory 304. The functions, acts or tasks may be independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

The computing device 300 may further include a display 314, such as a liquid crystal display (LCD), an organic light emitting diode (OLED), a flat panel display, a solid state display, a cathode ray tube (CRT), a projector, a printer or other now known or later developed display device for outputting determined information. The display 314 acts as an interface for the user to see the functioning of the processor 302 and interact with the software (including the processor-executable instructions 324) stored in the memory 304 or in the drive unit 306.

The computing device 300 further includes an input device 312 configured to allow a user to interact with any of the components of the cone-beam computed tomography system 100. The input device 312 may be a number pad, a keyboard, or a cursor control device such as a mouse, a joystick, a touch screen display, a remote control or any other device operative to interact with the computing device 300.

The computing device 300, in other embodiments, includes a disk or optical drive unit 306 to accessibly interpret computer-readable medium 322, on which software embodying algorithms or processor-executable instructions 324 are embedded. The algorithms or processor-executable instructions 324 perform one or more of the methods or logic as described herein. The algorithms or processor-executable instructions 324 may reside completely, or at least partially, within the memory 304 and/or within the processor 302 during execution by the computing device 300. The memory 304 and the processor 302 also may include other forms or configurations of computer-readable media as discussed above.

The present disclosure contemplates a computer-readable medium 322 that includes processor-executable instructions 324 or receives and executes instructions 324 responsive to a propagated signal, so that a device connected to a network 130 may communicate voice, video, audio, images or any other data over the network 130. Further, the processor-executable instructions 324 may be transmitted or received over the network 130 via a communication interface 318. The communication interface 318 may be implemented in software or may be a physical connection in hardware. The communication interface 318 provides a connection with the network 130, external media, the display 314, or any other components in the cone-beam computed tomography system 100 or combinations thereof. In one embodiment, the connection with the network 130 is a physical connection such as a wired Ethernet connection or may be established wirelessly such as via a cellular telephone network (GSM, CDMA, etc.), an IEEE 802.11 (WiFi) network, an 802.16 (WiMax) network, an 802.20 (wireless broadband) network, and a Bluetooth or personal area network (PAN). The network 130 in other embodiments can be a public network, such as the Internet, a private network, such as an intranet, or combinations thereof, and may utilize a variety of networking protocols now available or later developed including, but not limited to TCP/IP based networking protocols.

The computer-readable medium 322 may be a single medium or may comprise multiple mediums such as a centralized or distributed database and/or associated caches and servers that store one or more sets of instructions. The term "computer-readable medium" is generally utilized to describe any medium that may be capable of storing, encoding or carrying an algorithm or set of instructions for execution by a processor or that may cause a computer system to perform any one or more of the methods or operations disclosed herein.

The computer-readable medium 322 may include a solid-state memory such as a memory card or other package that houses one or more non-volatile read-only memories. The computer-readable medium 322 further includes or encompasses random access memory or other volatile re-writable memory. Additionally, the computer-readable medium 322 may include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that may be a tangible storage medium. The present disclosure may be considered to include any one or more of a computer-readable medium or a distribution medium and other equivalents and successor media, in which data or instructions may be stored.

In other embodiments, dedicated hardware implementations such as application specific integrated circuits (ASIC), programmable logic arrays (PLAs) and other hardware devices may be constructed to implement one or more of the methods described herein. Applications that include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit (ASIC). Accordingly, the present system may encompass software, firmware, and hardware implementations.

II. Recording and Motion Control

Figure 4:
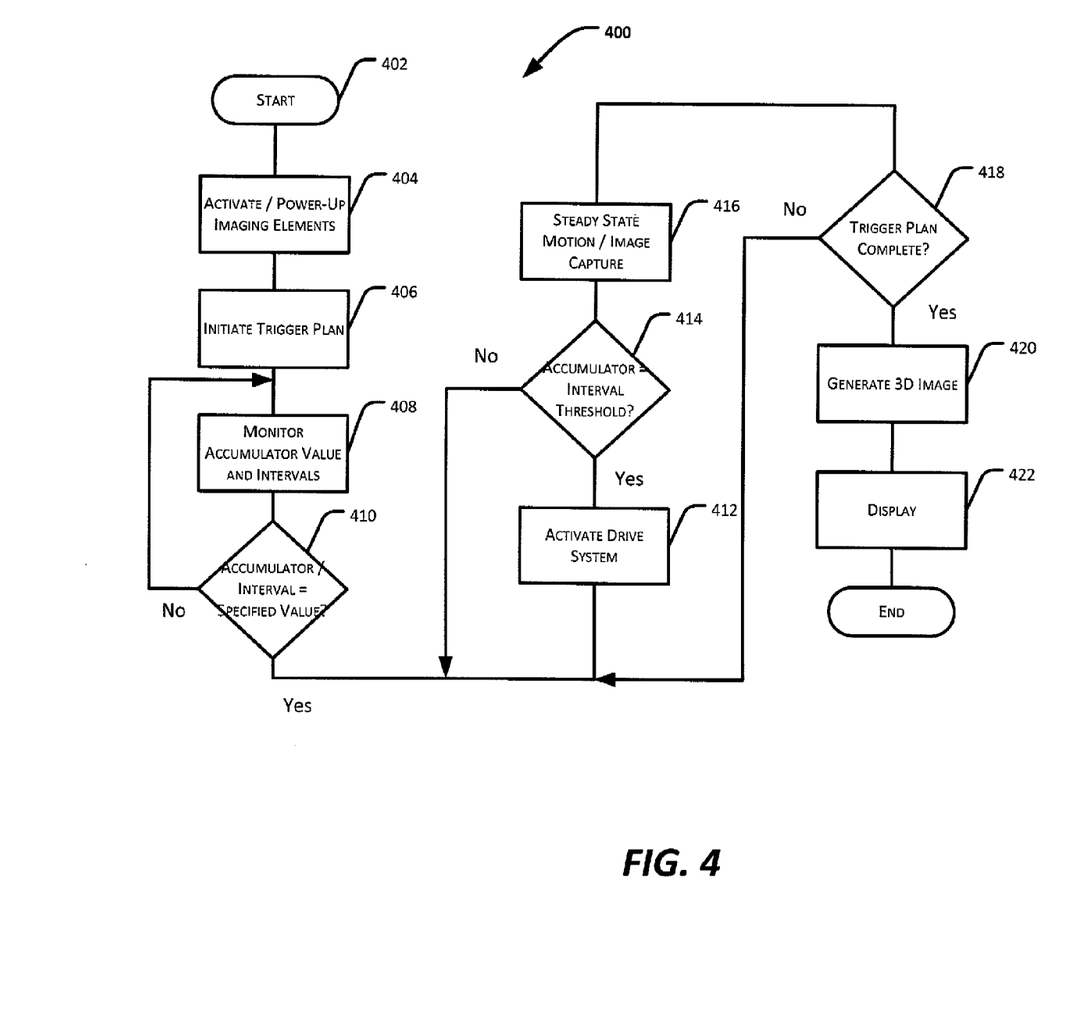
FIG. 4 is a flowchart of the operations and functions that may be implemented by the exemplary cone-beam computed tomography system shown in FIG. 1.

FIG. 4 is a flowchart illustrating one embodiment of the image recording and motion control functionality of the exemplary cone-beam computed tomography system 100. In particular, the functionality described with respect to the flowchart may be programmed or stored as a part of the processor-executable instructions 324 as the constant frequency control routine 400. In operation, the constant frequency control routine 400 may be stored in the memory 304 and executed by the processor 302. Alternatively, the constant frequency control routine 400 (see FIG. 3) may be implemented as hardware or other non-transitory means.

The constant frequency control routine 400 activates, as illustrated in the flowchart shown in FIG. 4, in response to a user command or directive to power-up and/or start the imaging process (step 402). The routine 400 activates the radiation source 202 and the radiation detector 204 as well as the associated drive systems 250 and 260 for operation (step 404). At this point and as shown in FIG. 4, the routine 400 at time zero ($t_0$) directs the controller 216 to initiate or activate an applicable tripping or trigger plan (step 406). The trigger plan may be stored locally in the memory of the controller 216 or may be stored in the data store 120 and accessible via the network 130. The trigger plan specifies the number of oscillations or pulses that are to be counted or accumulated by the motor driver 210 in order for the motor 208 to drive the radiation source 202 and radiation detector 204 combination to a specific location in order to capture an image of the object.

The routine 400 and the controller 216 delay motion of the first drive system 250 and operation of the radiation source 202 and the radiation detector 204 until a specific number of pulses or oscillations has been detected and stored in a memory register or accumulator (step 408). In this exemplary embodiment, the controller 216 counts and stores the constant frequency signal between a first interval defined between an initial point zero ($p_0$) and a first point or period ($p_1$), and a second interval defined between the first point ($p_1$) and a second point ($p_2$) (see FIG. 5). Once the accumulator has stored or monitored the desired pulses or oscillations corresponding to the first and second intervals (step 410), the controller 216 may at point $p_2$ activate the first drive system 250 and translate the radiation source 202 and radiation detector 204 combination (step 412). Translation of the radiation source 202 and radiation detector 204 combination may continue until the second drive system 260 has reached steady state and stable operation. Steady state operation may be determined and measured with respect to a threshold value of oscillations or pulses or a number of intervals (e.g., the four intervals defined between $p_2$ and $p_6$) defined as a function of the constant frequency control signal (step 414). Once the specified threshold has been achieved and/or stored in the accumulator, the routine 400 operating in accordance with the trigger plan may activate the radiation source 202 and radiation detector 204 combination to collect and store image data describing the object (step 416). If the routine 400 determines that the trigger plan has not been completed and/or fully implemented (step 418), the process continues and the first drive system 250 is again activated to translate the position of the radiation source 202 and radiation detector 204 combination to the next desired imaging location (see step 412). However, if the routine 400 determines that the trigger plan has been fully executed, the multiple instances of two dimensional image data and signal information acquired in conjunction with the trigger plan and stored in the memory 304 may be manipulated and reconstructed to generate a three dimensional representation of imaged object (step 420). The reconstructed three dimensional image can subsequently be displayed via the display 314 and manipulated using one or more input devices 312 (step 422).

Figure 5:
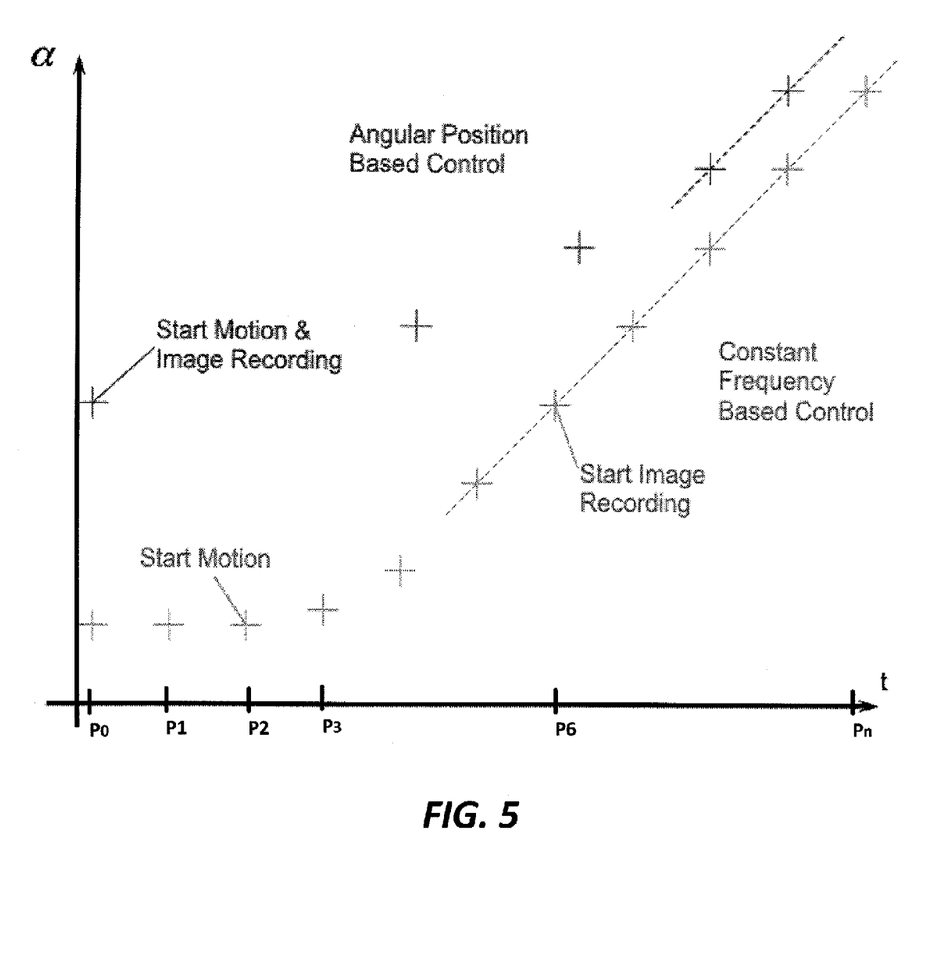
FIG. 5 is a chart depicting the angular motion versus time for both a convention cone-beam computed tomography system and a cone-beam computed tomography system configured according to the teaching and disclosure provided herein.

As FIG. 5 illustrates, the cone-beam computed tomography system 100 controlled via the constant frequency control routine 400 displays equidistant intervals and positioning while conventional systems utilizing angular positioning control display irregular intervals and positioning. The irregular and inconsistent image capture of conventional systems results in degraded accuracy when compared to the image capture realized by the exemplary constant frequency control.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed is:

1. A system for motion control of a cone-beam tomography recording device, the cone-beam tomography recording device comprising a paired radiation source and radiation detector, the system comprising:
   a drive system configured to position the paired radiation source and radiation detector relative to an object to be imaged;
   a controller in communication with the drive system and configured to direct operation of the drive system, wherein the controller is operable to:
      initiate a trigger plan operable as a function of a control signal having a constant frequency;
      activate the paired radiation source and radiation detector in accordance with the trigger plan, wherein the radiation source is configured to broadcast a radiation signal, and wherein the radiation detector is configured to record the broadcast radiation signal;
      drive, in response to the trigger plan, the drive system to a steady operating state derived as a function of the constant frequency;
      capture a plurality of broadcast radiation signals representative of a plurality of two dimensional images of the object, wherein the plurality of two dimensional images are captured at substantially equidistant positions relative to the object as defined by the trigger plan and as a function of the control signal; and
      generate a three dimensional representation of the object based on the plurality of two dimensional images.

2. The system of claim 1, wherein the trigger plan governs the generation and recordation of the broadcast radiation signal as a function of the constant frequency.

3. The system of claim 1, wherein the control signal is a stepper signal.

4. The system of claim 1, wherein the control signal is an oscillating signal having a fixed interval.

5. The system of claim 1, wherein the drive system includes a motor driver operable to interface with a positioning motor.

6. The system of claim 1 further comprising:
   a memory in communication with the controller,
   wherein the controller is further operable to:
      store each broadcast radiation signal of the plurality of broadcast radiation signals in the memory, wherein the memory is configured to indexably store each broadcast radiation signal of the plurality of broadcast radiation signals.

7. A method for motion control of a cone-beam tomography recording device, the method comprising:
   generating a constant frequency control signal;
   activating a radiation detector in accordance with a trigger plan, wherein the radiation detector is configured to record a broadcast radiation signal generated by a radiation source, and wherein the trigger plan directs the radiation detector to record a broadcast radiation signal as a function of the constant frequency control signal;
   driving, in response to the trigger plan, a drive system configured to position the radiation source and the radiation detector, wherein the drive system is operated as a function of the constant frequency control signal;
   activating the radiation source in accordance with the trigger plan when the drive system is determined to be operating in a steady state, wherein the radiation source generates the broadcast radiation signal as a function of the constant frequency control signal; and
   capturing a plurality of broadcast radiation signals at intervals defined by the trigger plan as a function of the constant frequency control signal.

8. The method of claim 7, wherein each broadcast radiation signal of the plurality of broadcast radiation signals corresponds to a two dimensional image of the object.

9. The method of claim 8 further comprising:
   generating a three dimensional representation of the object based on the plurality of two dimensional images.

10. The method of claim 7, wherein the constant frequency control signal is an oscillating signal occurring at a fixed interval.

11. The method of claim 7, wherein driving the drive system comprises using a motor driver configured to interface with a positioning motor.

12. The method of claim 7 further comprising:
   storing each recorded broadcast radiation signal in a communicatively coupled memory, wherein the memory is configured to retrievably store the constant frequency control signal associated with the generation and recordation of the broadcast radiation signal.

13. A system for motion control of a cone-beam tomography recording device, the cone-beam tomography recoding device comprising a paired radiation source and radiation detector, the system comprising:
   a position motor;
   a drive system including a motor driver operable to interface with the positioning motor, wherein the positioning motor is configured to:
      position the paired radiation source and radiation detector relative to an object to be imaged; and a controller in communication with the motor driver and configured to direct operation of the positioning motor via the motor driver, wherein the controller is configured to:
  implement a trigger plan operable as a function of a control signal having a constant frequency;
  activate the paired radiation source and radiation detector in accordance with the trigger plan;
  drive, in response to the trigger plan, the positioning motor to a steady operating state determined as a function of the constant frequency; and
  capture a plurality of two dimensional images based on corresponding broadcast radiation signals, wherein the plurality of two dimensional images are acquired at equidistant positions defined by the trigger plan and as a function of the control signal; and
  generate a three dimensional representation of the object based on the plurality of two dimensional images.

14. The system of claim 13, wherein the trigger plan governs the generation and recordation of the broadcast radiation signal as a function of the constant frequency.

15. The system of claim 13, wherein the radiation source is configured to broadcast a radiation signal, and
  wherein the radiation detector is configured to record the broadcast radiation signal.

16. The system of claim 13, wherein the control signal is an oscillating signal having a fixed interval.

17. The system of claim 13, further comprising a memory in communication with the controller,
  wherein the controller is further operable to:
    store each broadcast radiation signal of the plurality of broadcast radiation signals in the memory, wherein the memory is configured to indexably store each broadcast radiation signal of the plurality of broadcast radiation signals.

* * * * *